United States Patent [19]
Bryant

[11] Patent Number: 5,113,081
[45] Date of Patent: May 12, 1992

[54] WEB INSPECTION SYSTEM AND METHOD WITH EXPOSURE, DETECTION AND SAMPLING MEANS

[75] Inventor: Steven M. Bryant, Holley, N.Y.

[73] Assignee: Eastman Kodak Company, Rochester, N.Y.

[21] Appl. No.: 634,982

[22] Filed: Dec. 27, 1990

[51] Int. Cl.⁵ .............................................. G01N 21/86
[52] U.S. Cl. .................................... 250/571; 356/444
[58] Field of Search ............... 250/571, 559; 356/443, 356/444; 354/297

[56] References Cited

U.S. PATENT DOCUMENTS

| | | | |
|---|---|---|---|
| 4,176,964 | 12/1979 | Knör et al. | 356/444 |
| 4,277,177 | 7/1981 | Larsen et al. | 250/571 |
| 4,931,657 | 6/1990 | Houston et al. | 250/571 |

Primary Examiner—David C. Nelms
Assistant Examiner—T. Davenport
Attorney, Agent, or Firm—Francis H. Boos, Jr.

[57] ABSTRACT

A web of photographic film or the like having an optical property to be inspected and measured (such as exposure density or reflectance) is transported through a flasher chamber at a predetermined nominal speed and is exposed to radiation in the flasher to produce a series of longitudinally spaced, transversely oriented exposure bands separated by unexposed bands on the web. The transport speed of the web through the exposure chamber is selected for a given exposure period for each band such that the web moves only a minor fraction of the longitudinal width of each band during exposure of the band. Subsequent inspection of the web, for example, in a densitometer, produces a pulsed output signal waveform in which the peak amplitudes of the pulses are proportional to the optical property being measured independent of any perturbations in transport speed of the web through the exposure chamber.

8 Claims, 5 Drawing Sheets

WEB INSPECTION SYSTEM AND METHOD WITH EXPOSURE, DETECTION AND SAMPLING MEANS

FIELD OF INVENTION

This invention relates to the field of web inspection and more particularly to apparatus for exposing a moving web to light flux to determine the existence of periodic or random fluctuations in an optical characteristic of the web, such as non-uniformities in transmittance or reflectance of the web. It is of particular interest for use as a neutral density flasher system for measuring exposure density of photographic film or paper.

BACKGROUND OF INVENTION

In the production of coated webs, such as photographic films and papers, it is necessary to perform measurements as part of the production process to ascertain that the coatings are uniform along the length of the web. It is well known to use what is generally called a neutral density flasher for this purpose. A neutral density flasher is apparatus that is used to expose an elongated length of the film to a constant intensity, white light source so that later examination with a densitometer, after processing of the film, can determine variations such as streaks, spots and repetitive anomalies in the film. A particular example when detection of repetitive anomalies is particularly important is in the case of movie film for which repetitive variations in film density are of concern since these defects can cause flickering, a phenomenon which is readily observable to the human eye as the film is played.

Existing neutral density flashers are illustrated schematically in FIG. 1 as including a light exposure box 10 positioned between film supply and takeup reels 12 and 14. As an unexposed strip of film 16 passes over idler/tensioning rollers 17 through the exposure box at some fixed speed, it is exposed to radiation such as a constant intensity white light source 18 to uniformly expose an elongated length of the film, typically upwards of 100'. After subsequent processing (developing) of the film, it is then passed through a densitometer to measure the film density along its exposed length to determine the existence of any undesired variations in the film density characteristic that might be cause for rejecting the film batch from which the test strip was taken. In the case of photographic paper, reflectance rather than density would be the measured characteristic.

Flashers of this type have the problem that repetitive variations in density or reflectance of the film or paper are difficult to isolate. This is because the flasher itself can induce its own variations during the exposure process. For example, reel drive speed variations and motor and roller vibrations can disrupt the constant speed of the film passing through the exposure box causing film jitter which, in turn, adversely affects the total integrated exposure of the film strip over successive increments of the film. Attempts to minimize the effects of frequency variations include using lower light source intensities and longer time exposure to smooth out the fluctuations. To reduce the effect of motor and roller vibrations, high grade bearings and highly stable motor controls are used which significantly increases the complexity and cost of such flasher systems.

It is therefore an object of the invention to provide a web inspection system and a corresponding inspection method that is simpler and more cost effective than systems and methods using flashers of the type described above.

It is a further object of the invention to provide a web inspection system and method utilizing web flasher apparatus that give selected web characteristic measurements, either density or reflectance, that are independent of system induced anomalies such as drive speed variations and film jitter caused by motor and roller vibrations.

SUMMARY OF INVENTION

In accordance with the invention therefore, rather than expose or flash the web or film strip with a constant source of light or other suitable radiation continuously along an elongated dimension of the web, a flasher is provided that periodically exposes the web to the radiation source to produce a series of longitudinally spaced transverse exposure bands. These exposure bands, following suitable processing in the case of photographic film, can then be exposed to a second source of radiation and the transmitted or reflected radiation sensed to develop a pulsed signal waveform in which the peak amplitudes of the pulses corresponding to the transverse exposure bands are proportional to the optical property of the web material to be measured, such as exposure density in the case of photographic materials such as film or print paper. Since the width of the exposure band, in the longitudinal transport direction of the web through the exposure chamber, is extremely short, any variations in speed of the web such as jitter caused by drive motors or rollers has no affect on the amplitude of the pulses produced from the bands. Consequently, sampling the central portions of each of the pulses provides a reliable representation of the optical property of the web sought to be measured that is independent of the web speed.

DETAILED DESCRIPTION

Figure 1:
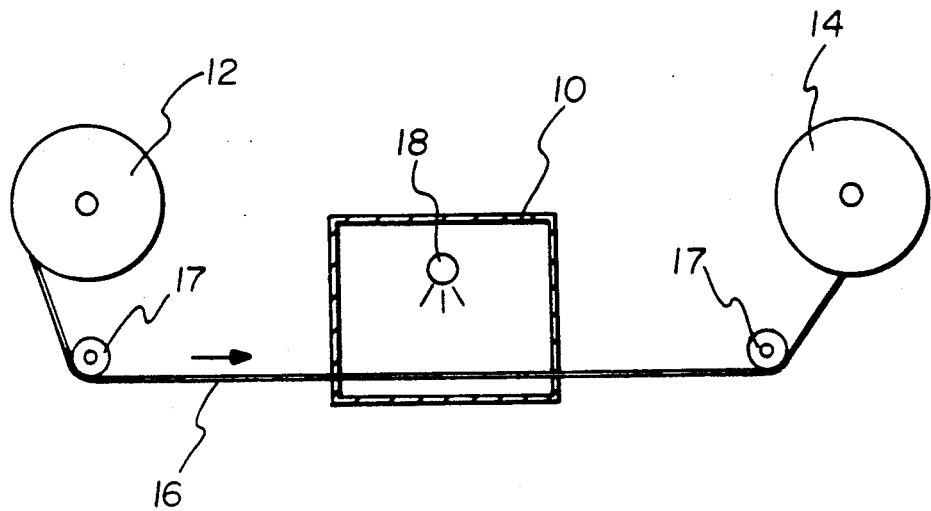
FIG. 1 is a schematic representation of a prior art type of neutral density flasher as used in photographic film production.
Figure 2:
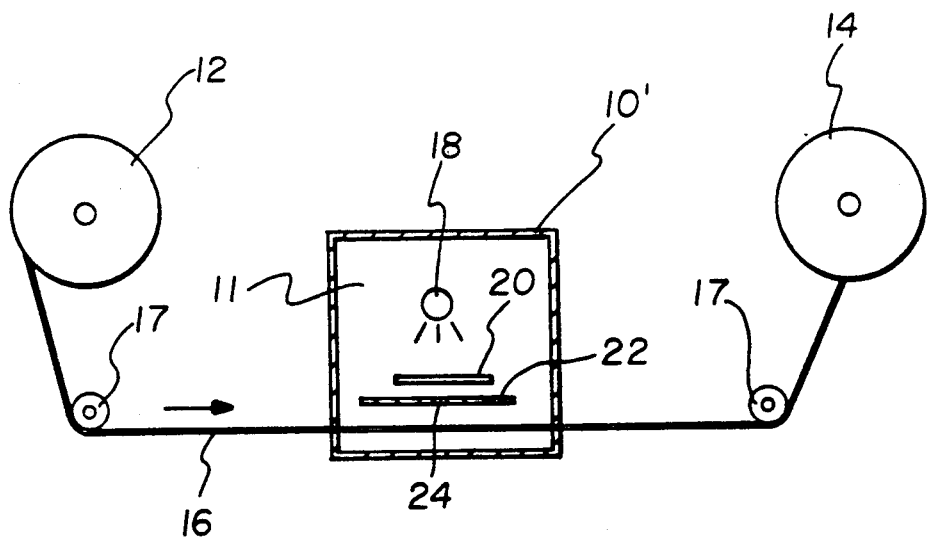
FIG. 2 is a schematic representation of a neutral density flasher apparatus useful in the web inspection system of the present invention.

Referring to FIG. 2, the web inspection system of the invention will described in the context of a neutral density flasher used in connection with measurement of exposure density of photographic film strips. Thus, the neutral density flasher illustrated in FIG. 2, includes a housing 10' which defines an exposure chamber 11 through which a film strip 16 is transported at a predetermined nominal speed, e.g. 100 ft/min, from supply reel 12 to take-up reel 14 after passing over intermediate rollers 17. A drive motor, not shown, is coupled in known manner to takeup reel 14 to pull the film 16 through the exposure chamber at the desired nominal speed. Because of the nature of the present invention, it is not necessary to provide expensive controlled speed motor drives or motor and roller bearings to precisely maintain the nominal speed and eliminate jitter of the film of the film transport through the exposure chamber.

Figure 3:
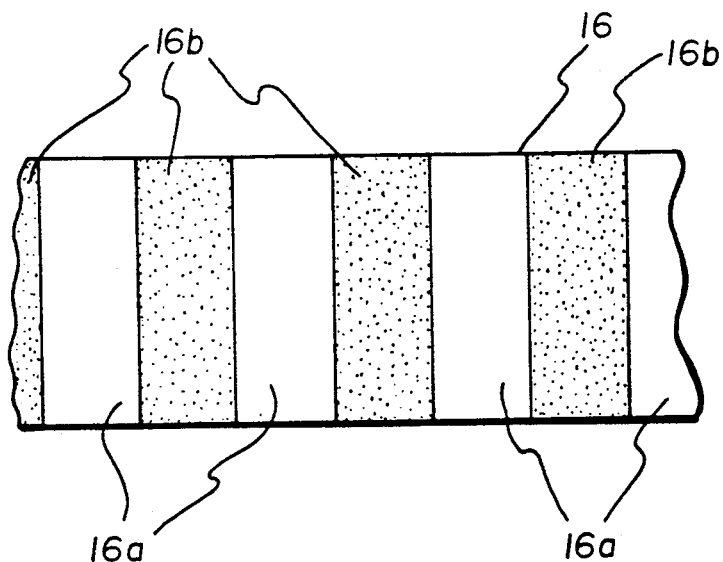
FIG. 3 is a plan view of a film strip exposed in the flasher apparatus of FIG. 2.
Figure 4:
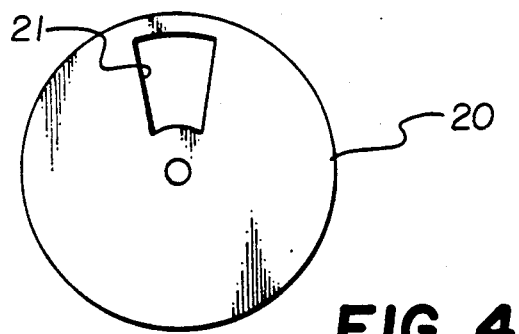
FIG. 4 is a plan view of a rotating shutter wheel useful in the flasher apparatus of FIG. 2.
Figure 5:
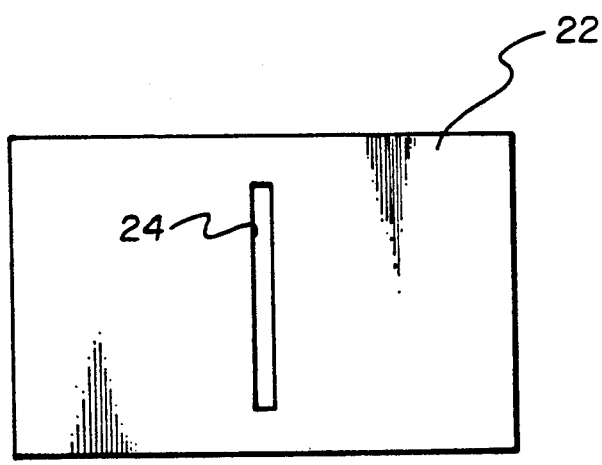
FIG. 5 is a plan view of an apertured mask useful in the flasher apparatus of FIG. 2.

Light 18 is positioned within exposure chamber 11 and comprises a source of first radiation for exposing film strip 16 to fix an optical characteristic of the film strip, in this case its exposure density. As is known, the exposure density of the film is a function of the light flux reaching the film times the duration of the exposure. In accordance with a particular feature of the invention, means are provided in the exposure chamber for sequentially exposing longitudinally spaced, transverse bands 16a on the film 16 (FIG. 3) interspersed with bands 16b of unexposed regions on the film. Such means may comprise a rotating shutter wheel 20 (FIG. 4) provided with a radial aperture 21 and a mask 22 (FIG. 5) provided with an elongated aperture 24 having its elongated dimension oriented transverse to the transport direction of the film 16 through the exposure chamber.

Figure 6:
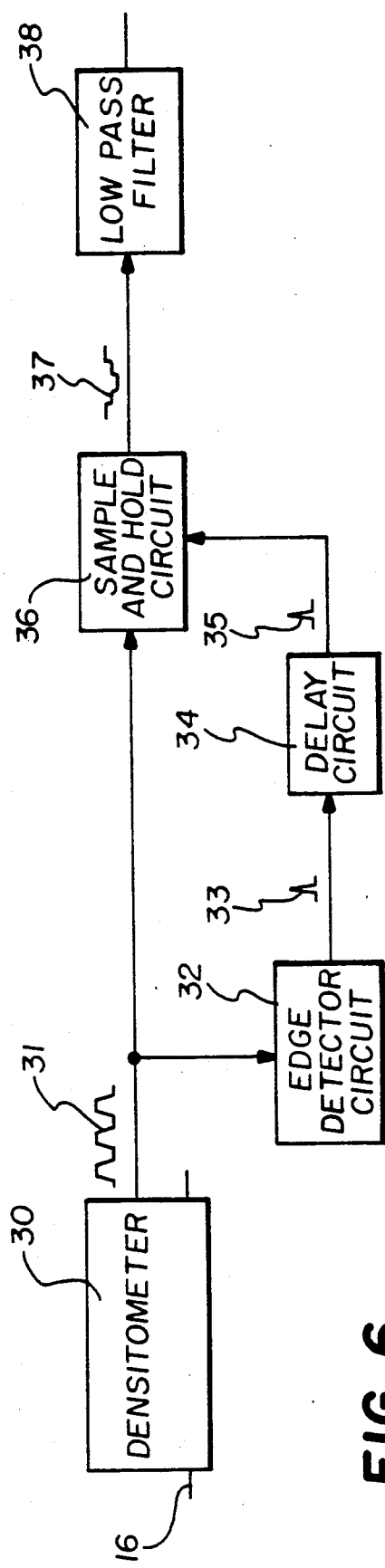
FIG. 6 is a schematic of signal sampling means useful in the web inspection system of the invention.

Having exposed an indeterminate length of the film strip 16 in the flasher apparatus of FIG. 2 to provide the series of spaced apart exposure bands 16a, the system of the invention is further provided with means for subsequently exposing the film strip to second radiation and for sensing the amount of transmitted or reflected radiation to produce a pulsed signal waveform having peak amplitudes proportional to the transmitted or reflected radiation at each of the exposed and unexposed bands 16a and 16b. Referring to FIG. 6, such means is comprised of a conventional densitometer 30 which produces at its output the pulsed signal 31 shown in FIGS. 7 and 8. It will be appreciated that, in the case of photographic film as used in this example, the film strip is processed in a conventional film development process after exposure in the flasher apparatus to convert the latent image exposure bands 16a into visible image bands prior to being sensed by the densitometer.

Figure 7:
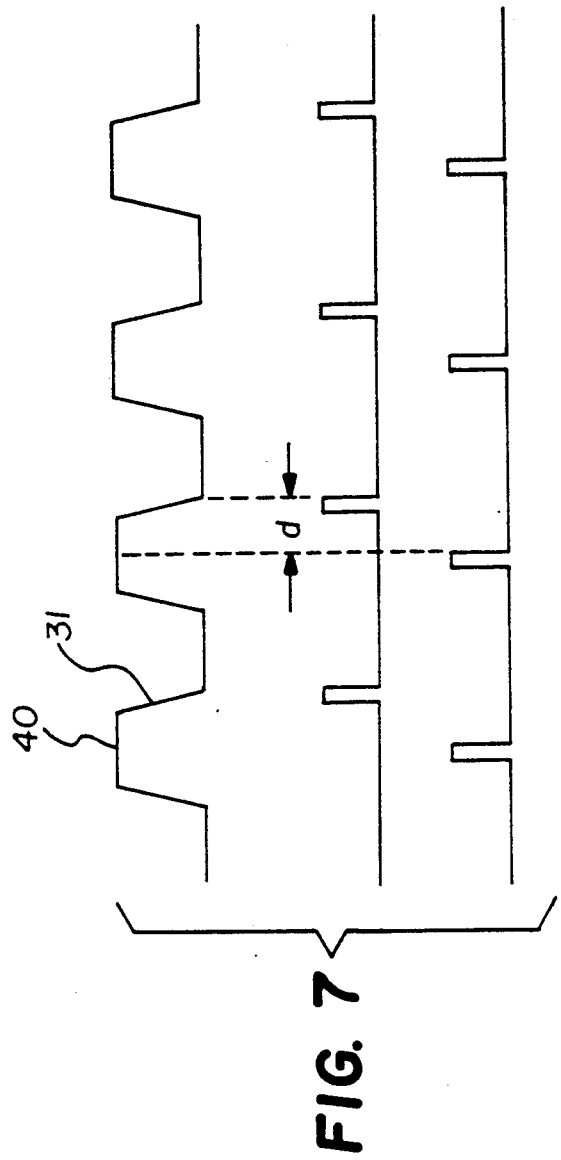
FIGS. 7 and 8 illustrate signal waveforms useful in explaining the operation of the web inspection system of the invention.
Figure 8:
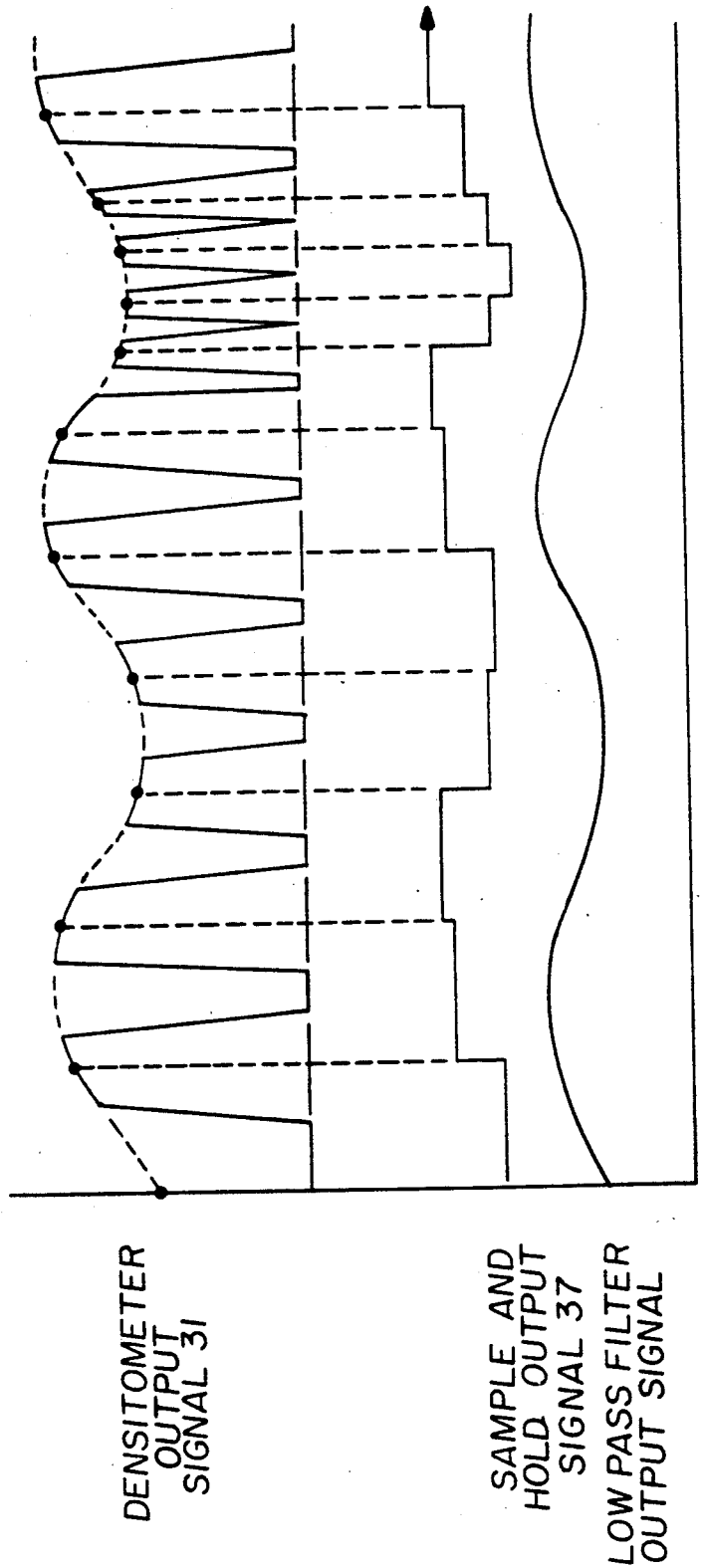

The system of the invention further includes means for sequentially sampling the peak amplitudes of the pulsed signal waveform from the densitometer to generate an output signal having components thereof which are representative of the web optical property to be measured and which are independent of any variations in the nominal speed at which the film was transported through the flasher exposure chamber 11. As seen in FIG. 6, such means may include edge detector circuit 32 coupled to the output of densitometer 30. Detector 32 operates in known manner to derive a sampling pulse waveform 33 coincident with the leading edges of the pulses of waveform 31. These sampling pulses are then coupled to time delay circuit 34 which inserts a time delay, d, as needed to align the sampling pulses 33 with the central portion of the density representative pulses in waveform 31. These delayed sampling pulses 35 are then applied to a conventional sample and hold circuit 36 which operates to derive an analog output waveform 37, the amplitude of which is proportional to the peak amplitudes 40 of the pulses in waveform 31. This waveform may then be passed through a low pass filter 38 to generate an analog signal suitable for application to video monitor circuits for visual inspection of the density readings for the film strip 16. Alternatively, waveform 37 may be applied to an analog-to-digital converter to convert the waveform 37, in a conventional manner, into digital format suitable for application to a microcomputer which can be programmed in known manner to perform signal analysis of the components of interest in densitometer signal 31. In FIG. 7, the densitometer output signal waveform 31 has peak amplitudes 40 which are constant in value as would be the case for a film strip having a constant neutral density along its length. In FIG. 8, there is illustrated a densitometer output signal 31 having varying peak amplitude components caused by undesired density variations in the film. After sampling, these components appear as varying amplitude levels in signal 37 which are converted by the low pass filter circuit 38 to the varying LPF analog signal illustrated in the figure. It should be noted that the waveforms of FIG. 8 are not drawn to scale, being exaggerated for illustrative purposes.

In order to be able to detect repetitive anomalies in the optical characteristic of interest, e.g. exposure density, it is necessary that the exposure repetition rate of the flasher apparatus be selected with a view to the highest repetition rate or spatial frequency of the anomaly to be detected. For example, it is generally known in the production of certain photographic films that the highest spatial frequency of exposure density variations that are normally of concern is about 100 Hz for films travelling at 100 ft/min, corresponding to a repetition period of 0.2 inch on the film. The well known Nyquist sampling theory states that detection of a signal occurring at a given frequency must be sampled at a minimum sampling rate of two times the frequency of the signal being detected. Consequently, for a neutral density flasher constructed to detect density variations up to 100 Hz, a minimum flashing frequency of 200 Hz would be required which corresponds to a rotational speed of 12,000 rpm for the single aperture rotating shutter 20 of FIG. 4. Increasing the number of apertures will reduce the rotational speed proportionately. The duration of each flash exposure, and the corresponding flash duty cycle is determined by the angular width of the shutter aperture 21.

Figure 9:
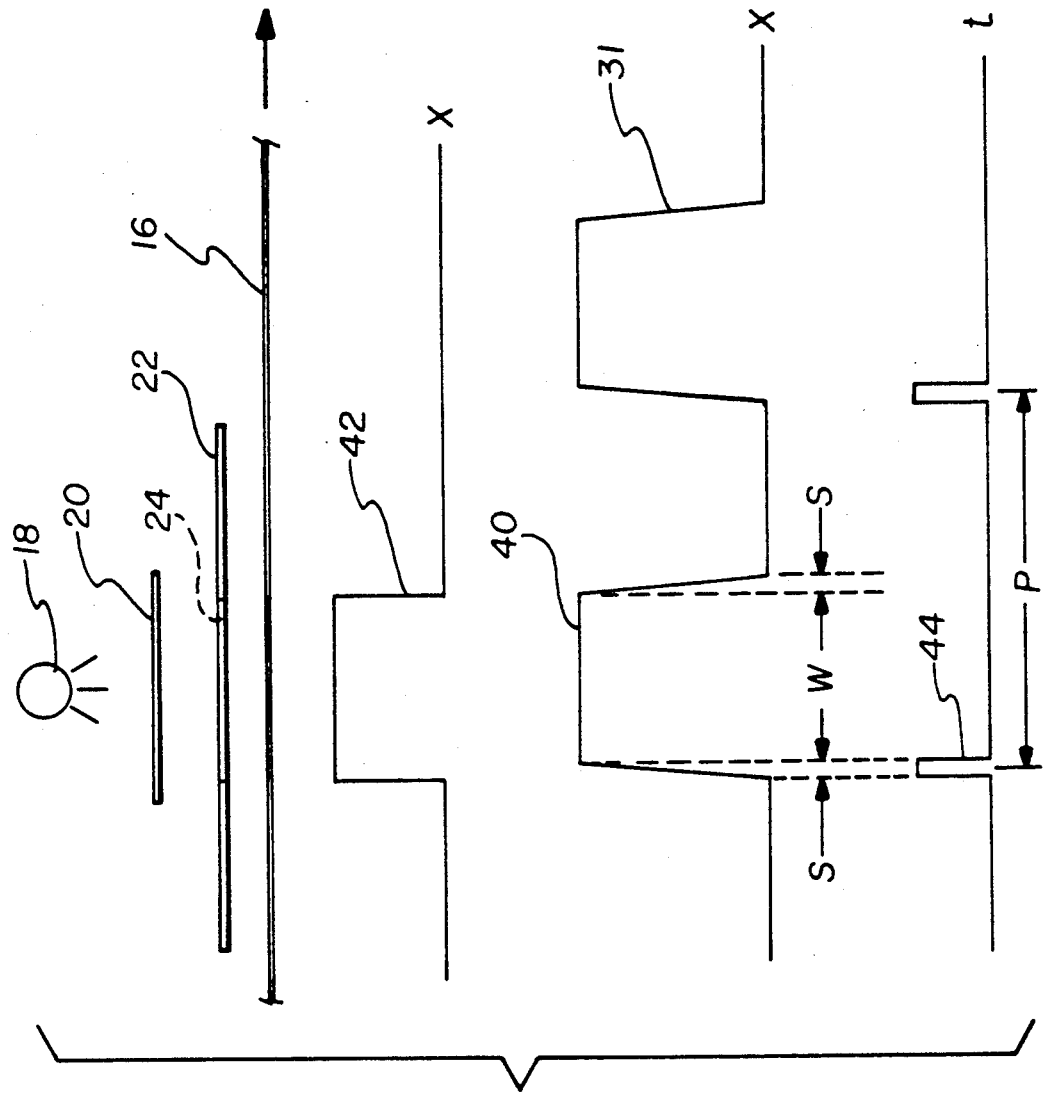
FIG. 9 is a combined schematic illustration of the flasher apparatus of FIG. 2 signal waveform useful in explaining the operation of the invention.

For a given exposure duration and a given width of mask aperture 24 in the film longitudinal direction, the corresponding longitudinal width of the exposure bands 16a is a function of the speed of the film through the exposure chamber 11. This is best seen with reference to FIG. 9 which illustrates the effect of film movement through the exposure chamber on the flasher induced exposure bands produced by the uniform spatial flux distribution pattern 42 on the film 16 as represented by output pulse waveform 31 from densitometer 30. During the brief periods in which film 16 is exposed to the uniform temporal flux distribution 44 from light source 18, the film moves a distance S. As a result, the longitudinal width of the exposure band is comprised of leading and trailing portions, S, having longitudinal dimensions determined by the film transport speed, plus a central portion of longitudinal dimension W. This central dimension, W, is also proportional to film transport speed. More importantly, however, the central portion has a relatively constant peak (plateau) amplitude that is proportional solely to the light flux (a constant over the dimension W) and the density of the film and is independent of the film transport speed. Consequently, by choosing a film transport speed that restricts the velocity-dependent leading and trailing portions, S, of the exposure bands to a minor fraction of the total longitudinal width of the bands, for example less than 20% and preferably less than 10%, a firly broad protion of the pulse remains that can be sampled to provide film density information that is independent fo noise interference in the signal caused by perturbations in film transport speed through the exposure chamber. As a result, the method of film density measurement with the system and apparatus of this invention provides an accurate representation of the true density conditions of the film without the need for the use of costly precision motor and roller drive components.

The invention has been described in detail with particular reference to a presently preferred embodiment, but it will be understood that variations and modifications can be effected within the spirit and scope of the invention. As an example, a strobed light source might be used in place of the light and rotating shutter combination of the embodiment of FIG. 2.

What is claimed is:

1. A process for measuring a radiation sensitive optical property of a web of material comprising the steps of:
    providing a strip of indeterminate length of such web material;
    sequentially exposing longitudinally spaced transverse bands of said strip to first radiation for brief periods of time to thereby fix said optical property in each of the transverse bands while transporting said strip longitudinally at a predetermined nominal speed selected so that said strip moves only a minor fraction of the width of each band during the exposure of each band;
    subsequently exposing the strip to second radiation and sensing the amount of transmitted or reflected radiation to produce a pulsed signal waveform having peak amplitudes proportional to such transmitted or reflected radiation at each of said bands;
    sequentially sampling the peak amplitudes of said pulsed signal waveform to generate an output signal having components thereof which are representative of the optical property of the web material independent of variations from the predetermined nominal speed at which the strip is transported during exposure to said first radiation.

2. The process according to claim 1 in which the web is a photographic material such as film or print paper and the optical property is exposure density of the material and in which the process includes the step of processing the photographic material after exposure to the first radiation to fix the exposure density of the material.

3. A web inspection system for measuring a radiation sensitive optical property of a web of material, the system comprising:
    a housing defining an interior exposure chamber;
    means for transporting a strip of said web material of indeterminate length through said housing at a predetermined nominal speed;
    a source of first radiation positioned within said exposure chamber;
    means in said exposure chamber for sequentially exposing longitudinally spaced, transverse bands of said strip to said radiation source, said predetermined nominal speed being such that said strip moves only a minor fraction of the longitudinal width of each band during exposure of each band;
    means for subsequently exposing the strip to second radiation and for sensing the amount of transmitted or reflected radiation to produce a pulsed signal waveform having peak amplitudes proportional to such transmitted or reflected radiation at each of said bands;
    means for sequentially sampling the peak amplitudes of said pulsed signal waveform to generate an output signal having components thereof representative of the optical property of the web material independent of variations from the predetermined nominal speed at which the strip is transported during exposure to said first radiation.

4. The system of claim 3 in which said web is a web of photographic material and the optical property is exposure density of the photographic material and in which the system further includes means for processing the exposed photographic material to fix the exposure density of the material.

5. The system of claim 3 in which the means for periodically exposing the web to the first radiation includes a mask having an elongated relatively narrow aperture with the elongated dimension of the aperture oriented transverse to the longitudinal transport direction of the web and includes a shutter for periodically exposing the web to the first radiation through the elongated aperture of the mask.

6. Flasher apparatus for exposing an elongated web of material to radiation prior to measurement of a radiation sensitive optical property of the web, the apparatus comprising:
    a housing defining an interior exposure chamber;
    a source of radiation in the exposure chamber;
    means for limiting exposure of the source of radiation to the web to a series of longitudinally spaced transverse exposure bands separated by unexposed bands.

7. Flasher apparatus for exposing an elongated web of material to radiation prior to measurement of a radiation sensitive optical property of the web, the apparatus comprising:
    a housing defining an interior exposure chamber adapted to receive a strip of indeterminate length of said web for transport therethrough at a predetermined nominal speed;
    a source of radiation in said exposure chamber adapted to fix said optical property of the web material by exposure of the radiation to the web material;
    a mask having an elongated relatively narrow aperture with the elongated dimension of the aperture oriented transverse to the longitudinal transport direction of the web through the exposure chamber;
    and a shutter for periodically exposing the web to the radiation source through the elongated aperture of the mask;
    whereby a series of longitudinally spaced transverse radiation exposure bands can be produced on the web.

8. Flasher apparatus according to claim 7 in which the width of the aperture in the longitudinal transport direction of the web through the exposure chamber is such, relative to the nominal speed of web transport through the chamber, as to result in said web strip moving only a minor fraction of the width of each band during the exposure of each band.

* * * * *